United States Patent
Muratore et al.

(10) Patent No.: US 9,051,531 B2
(45) Date of Patent: Jun. 9, 2015

(54) CYCLOALKANE ALDEHYDES, METHOD FOR PREPARING SAME, AND USE THEREOF IN THE PERFUME INDUSTRY

(71) Applicant: V. Mane Fils, Bar sur Loup (FR)

(72) Inventors: Agnès Muratore, Chateauneuf (FR); Caroline Plessis, Chateauneuf (FR); Jean-Jacques Chanot, Speracedes (FR)

(73) Assignee: V.MANE FILS, Bar sur Loup (FR)

( * ) Notice: Subject to any disclaimer, the term of this patent is extended or adjusted under 35 U.S.C. 154(b) by 0 days.

(21) Appl. No.: 14/346,285

(22) PCT Filed: Oct. 9, 2012

(86) PCT No.: PCT/IB2012/055447
§ 371 (c)(1),
(2) Date: Mar. 20, 2014

(87) PCT Pub. No.: WO2013/054253
PCT Pub. Date: Apr. 18, 2013

(65) Prior Publication Data
US 2014/0221503 A1   Aug. 7, 2014

(30) Foreign Application Priority Data
Oct. 11, 2011  (FR) .................................. 11 59180

(51) Int. Cl.
C07C 47/00  (2006.01)
C07C 47/225  (2006.01)
C11B 9/00  (2006.01)

(52) U.S. Cl.
CPC ............... *C11B 9/003* (2013.01); *C07C 47/225* (2013.01); *C07C 2101/08* (2013.01); *C07C 2101/14* (2013.01); *C07C 2101/18* (2013.01)

(58) Field of Classification Search
CPC .. C07C 47/00; C07C 47/225; C07C 2101/08; C07C 2101/14; C07C 2101/18; C11B 9/003
USPC ................ 568/420; 512/27; 510/102
See application file for complete search history.

(56) References Cited

U.S. PATENT DOCUMENTS 3,517,031 A   6/1970  Beereboo et al.

FOREIGN PATENT DOCUMENTS

| CN | 1169416 | | 1/1998 |
| DE | 1193490 | * | 1/1964 |
| DE | 19817042 A1 | | 10/1999 |
| EP | 1136481 A1 | | 9/2001 |
| EP | 1930317 A1 | | 6/2008 |
| FR | 1367793 A | | 7/1964 |
| FR | 2005165 A1 | | 12/1969 |
| FR | 2038865 A5 | | 1/1971 |
| GB | 1281813 | | 7/1972 |

OTHER PUBLICATIONS

Giersch et al, Helv. Chim. Acta, 2004, 87(7), 1697-1703.*
RN 111998-18-6, 1987.*
RN 4744-87-0, 1984.*
RN 4401-29-0, 1984.*
Sell, Angew. Chem, Int. Ed. 2006, 45, 6254-626.*
Tietze et al, Chem. Ber. 121, 499-506 (1988).*
Bedel, Christian, International Search Report prepared for PCT/IB2012/055447 as mailed Feb. 20, 2013, 3 pages.

* cited by examiner

*Primary Examiner* — Shailendra Kumar
(74) *Attorney, Agent, or Firm* — B. Aaron Schulman, Esq.; Stites & Harbison, PLLC.

(57) ABSTRACT

The invention relates to a compound of general formula I represented below:

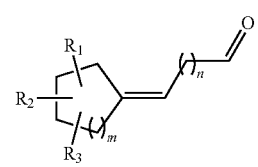

wherein:
R1, R2 and R3 each independently represent a hydrogen atom or saturated or unsaturated, branched or non-branched C1 to C5 alkyl group;
m is an integer between 1 and 4;
n is an integer between 2 and 4;
characterized in that the ring is saturated and comprises from 5 to 8 carbons, that the total number of carbons of the ring and of the radicals R1, R2 and R3 is between 7 and 11
and it being understood that said compound of formula (I) is not:
6-cycloheptylidenehexanal
4-(4-methylcyclohexylidene)-butanal
4-(4-tert-butylcyclohexylidene)-butanal
4-(3,3,5-trimethylcyclohexylidene)-butanal
as well as a method of synthesizing said compounds, and their uses in perfumery.

14 Claims, No Drawings

CYCLOALKANE ALDEHYDES, METHOD FOR PREPARING SAME, AND USE THEREOF IN THE PERFUME INDUSTRY

This application is a 371 of PCT/IB2012/055447, filed on Oct. 9, 2012.

The present invention relates to novel cycloalkane aldehyde compounds, their method of preparation and their use in the chemical industry, and in particular in perfumery, cosmetics, and in the detergents industry, said compounds having a special fragrance.

The perfume and flavourings industry is always searching for novel organoleptic compounds which exhibit an intense olfactory potency, whilst keeping production costs as low as possible. Some types of organoleptic compounds are more difficult to obtain than others, such as for example compounds which have marine and/or ozonic notes.

Amongst the compounds described in the prior art as having marine and/or ozonic notes are found, amongst the most used, benzodioxepinone derivatives (Helvetica Chimica Acta, 2007, 90, 1245-1265) such as Calone® or such as Azurone® (Givaudan) or 7-(3-methylbutyl)benzo[B][1,4]dioxepin-3-one (patent EP1136481).

Certain compounds from the aldehyde family are also known to exhibit this type of marine and ozonic notes. For example, it is possible to cite Melozone® (hexahydro-1-carboxaldehyde-4,7-methanoindane, patent DE19817042) which adds aldehyde notes in addition to the marine and ozonic notes. Or Geraldehyde® (5,9-dimethyl-4,8-decadienal, patents FR13677165 and FR2005165) which adds lemony notes, or Floralozone® (3-(4-ethylphenyl)-2,2-dimethylpropanal, Perfumer & Flavorist, 2009, 34, 18-19) which adds floral notes.

However, the compounds from the prior art which have an original marine or ozonic note have as the main disadvantage their high production cost, which is due notably to the number of synthesis steps, or to the cost of the raw materials. By way of illustration, the method of synthesising 7-methyl-3,4-dihydro-2H-1,5-benzodioxepin-3-one described in U.S. Pat. No. 3,517,031, comprises three steps, which is significant. Furthermore, the starting substrate, pyrocatechol, is a significantly expensive raw material. Likewise, the method of synthesising 3-methyl-6-(2,2,3-trimethylcyclopentyl)-hexanal (described as marine and ozonic in patent application EP1930317) comprises five synthesis steps from campholenic aldehyde.

In order to overcome the disadvantages of the prior art, the Applicant has unexpectedly discovered that cycloalkane aldehydes corresponding to the following general formula (I),

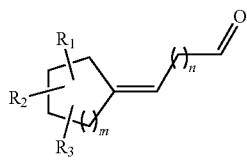

exhibited very intense marine and/or ozonic notes, and were obtained by means of a simple method performed in 2 steps from simple and inexpensive starting compounds.

Certain cycloalkane aldehydes corresponding to the preceding general formula (I) have been disclosed in the prior art but never as exhibiting marine and/or ozonic notes. These are the following compounds:

6-cycloheptylidenehexanal
4-(4-methylcyclohexylidene)-butanal
4-(4-tert-butylcyclohexylidene)-butanal
4-(3,3,5-trimethylcyclohexylidene)-butanal The compound 6-cycloheptylidenehexanal is described in an article by Tietze et al. (Chem. Ber. 121, 499-506, 1988) as a simple intermediate product lacking any direct industrial application, organoleptic or otherwise. As for the 3 other compounds disclosed in the prior art, they are all described in a patent by Naarden (FR2038865). In this patent, 4-(4-methylcyclohexylidene)-butanal is described as exhibiting fresh grassy notes which are reminiscent of those of lily of the valley; 4-(4-tert-butylcyclohexylidene)-butanal is described as having a pronounced floral fragrance; and 4-(3,3,5-trimethylcyclohexylidene)-butanal is described as having a woody floral fragrance which is strongly reminiscent of lily of the valley.

Therefore, none of the compounds corresponding to the general formula (I), and in particular none of the above 4 aldehyde compounds, is described in the prior art as exhibiting marine and/or ozonic notes.

The first object of the present invention is therefore a compound of the following general formula (I):

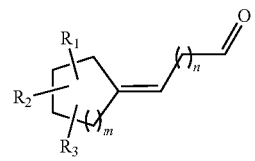

wherein:
R1, R2 and R3 each independently represent a hydrogen atom or a saturated or unsaturated, branched or non-branched $C_1$-$C_5$ alkyl group;
m is an integer between 1 and 4;
n is an integer between 2 and 4;
characterised in that the ring is saturated and comprises from 5 to 8 carbons, that the total number of carbons of the ring and of the radicals R1, R2 and R3 is between 7 and 11
and it being understood that said compound of formula (I) is not:
6-cycloheptylidenehexanal
4-(4-methylcyclohexylidene)-butanal
4-(4-tert-butylcyclohexylidene)-butanal
4-(3,3,5-trimethylcyclohexylidene)-butanal These compounds exhibit a marine, ozonic, watery, or even fruity (verging on melon, watermelon) or floral note which is very potent and diffusive, as well as a remarkable persistence. Furthermore, they are obtained through a method performed in 2 simple steps.

The term "$C_1$-$C_5$ alkyl" within the meaning of the present invention is understood to mean any monovalent radical derived from a saturated or unsaturated, linear or branched carbon chain containing 1 to 5 carbon atoms. The $C_1$-$C_5$ alkyls are preferably chosen from the methyl, ethyl, n-propyl, i-propyl, n-butyl, i-butyl, t-butyl and pentyl groups.

In a first embodiment, the present invention relates to compounds of general formula (I) wherein m is equal to 1, i.e. the ring is a cyclopentane.

In a second embodiment, the present invention relates to compounds of general formula (I) wherein n is equal to 4. A third embodiment consists of n being equal to 2.

In a preferred embodiment, the compounds according to the invention are chosen from 5-(2,4,4-trimethylcyclopentylidene)-pentanal, 6-(2,4,4-trimethylcyclopentylidene)-hexanal, 6-(2-methylcyclohexylidene)-hexanal, 6-(4-methylcyclohexylidene)-hexanal, 6-(4-tert-butylcyclohexylidene)-hexanal, 6-(4-tert-amylcyclohexylidene)-hexanal, 6-cyclooctylidenehexanal, 6-(3,3-dimethylcyclohexylidene) hexanal, 4-(2,4,4-trimethylcyclopentylidene)butanal, 4-(2-pentylcyclopentylidene)-butanal, 4-(3,3-dimethyl cyclohexylidene)-butanal, 5-(4,4-diethylcyclohexylidene)-pentanal and 5-cycloheptylidenepentanal.

More particularly, the invention relates to the compounds of formula (I) shown in Table 1 below.

TABLE 1

| Example | Structure | Olfactive description (at 5% by weight in dipropylene glycol, (DPG) |
|---|---|---|
| Example 1 | 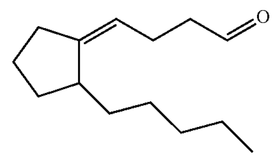 | Dried seaweed, mineral, aldehydic, fatty, citrusy (orange peel) |
| Example 2 | 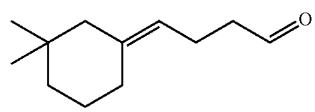 | Marine, watery, cucumber, green (apple), spicy (cardamom), aldehydic, flowery |
| Example 3 | 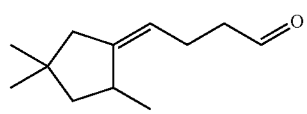 | Watery, cucumber, melon, ozonic, green, flowery |
| Example 4 | 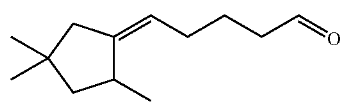 | Ozonic, hot iron, green, fatty, aldehydic |
| Example 5 | 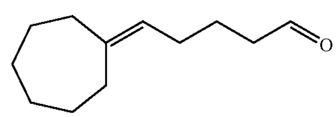 [SMILES: O=CCCCC=C1CCCCCC1] | Watery, cucumber, aldehydic, plastic, animal, leathery, gustatory (almondy, coumarin) |
| Example 6 | 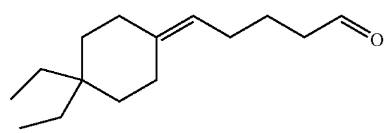 [SMILES: CCC1(CC)CCC(=CCCCC=O)CC1] | Ozonic, verging on dried seaweed, salty, flowery, fatty, green |
| Example 7 | 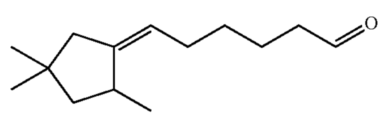 | Marine, watery, ozonic, green, aldehydic, coriander |
| Example 8 | 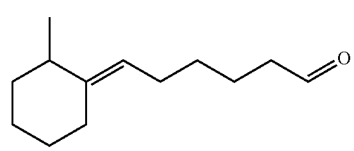 | Aldehydic, chlorinated, powdery, chocolate, animal |
| Example 9 | 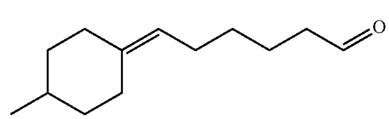 | Watery, chlorinated, aldehydic, gustatory (almond, coumarin), dusty |
| Example 10 | 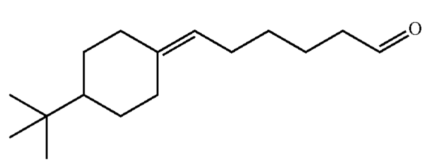 [SMILES: CC(C)(C)C1CCC(=CCCCCC=O)CC1] | Ozonic, aldehydic, fatty, powdery, chocolate |

TABLE 1-continued

| Example | Structure | Olfactive description (at 5% by weight in dipropylene glycol, (DPG) |
|---|---|---|
| Example 11 | (structure) | Marine, watery, mineral, seaweed |
| Example 12 | (structure) | Watery, chocolate, aldehydic, rancid, gustatory, woody |
| Example 13 | (structure) | Ozonic, watery, marine, green, aldehydic, aniseed, flowery |

The invention comprises all of the enantiomers and diastereoisomers of the compounds of formula (I), alone or in a mixture. In particular, the invention comprises the compounds represented by the general formula (I) in the form of mixtures of enantiomers in variable proportions, particularly racemic mixtures. The mixtures of enantiomers or mixtures of pure forms are produced by methods known to the person skilled in the art using, for example, optically enriched or optically pure starting products.

The compounds of formula (I) possess the advantage of being accessible by means of a preparation which is reliable and inexpensive, because it can be performed in 2 steps from low-cost starting compounds.

A second object of the present invention relates to a composition comprising at least one compound of general formula (I), with the exception of the compounds 6-cycloheptylidenehexanal, 4-(4-methylcyclohexylidene)-butanal, 4-(4-tert-butylcyclohexylidene)-butanal and 4-(3,3,5-trimethylcyclohexylidene)-butanal, in the form of an isomer or a mixture of isomers, of an enantiomer or of a mixture of enantiomers, or of a racemic mixture, or of a diastereoisomer or of a mixture of diastereoisomers.

According to one embodiment, the composition is characterised in that it further comprises at least one other fragrancing substance.

The effective quantity of the compounds of formula (I) according to the invention incorporated in the composition will vary depending on the nature of the composition, the required fragrancing effect, and the nature of the other compounds, fragrancing or not, that may be present, and will be able to be determined easily by the person skilled in the art, in the knowledge that it can vary within a very broad range, from 0.1 to 99% by weight, in particular from 0.1 to 50% by weight, and particularly from 0.1 to 30% by weight.

The invention also relates in particular to a cosmetic composition, particularly a face and body cream, talcum powder, hair or body oil, shampoo, hair lotion, bath salt, bath oil, shower gel, bath gel, toilet soap, body antiperspirant, body deodorant, lotions, shaving cream, shaving soap, cream, toothpaste, mouthwash, ointment, comprising at least one compound of formula (I), or at least one composition comprising at least one compound of formula (I), it being understood that the compounds of formula (I) are not the compounds 6-cycloheptylidenehexanal, 4-(4-methylcyclohexylidene)-butanal, 4-(4-tert-butylcyclohexylidene)-butanal and 4-(3,3,5-trimethylcyclohexylidene)-butanal.

The invention also relates to a cleaning product, particularly softener, detergent, washing powder, air freshener, comprising at least one compound of formula (I) or at least one composition comprising at least one compound of formula (I), it being understood that the compounds of formula (I) are not the compounds 6-cycloheptylidenehexanal, 4-(4-methylcyclohexylidene)-butanal, 4-(4-tert-butylcyclohexylidene)-butanal and 4-(3,3,5-trimethylcyclohexylidene)-butanal.

The compounds according to the invention can be used, alone or in combination, as they are or be incorporated in or on an inert support material or a material which can contain other active ingredients of the finished composition. A large variety of support materials can be used including, for example, polar solvents, oils, greases, finely divided solids, cyclodextrins, maltodextrins, gums, resins and any other known support material for such compositions.

A third object of the present invention relates to a method of preparing a compound of formula (I) in which a cycloalkanone and a phosphorus ylide undergo a Wittig reaction, followed by a reduction and/or oxidation step depending on the ylide used previously.

The method according to the invention comprises in particular the steps of:

i) adding a phosphorus ylide of formula (III) onto a cycloalkanone of formula (II), in accordance with a Wittig reaction:

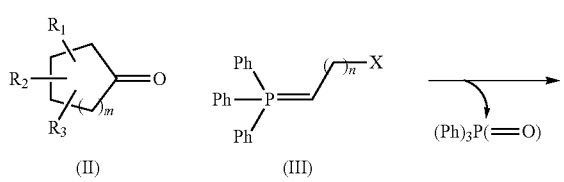

-continued

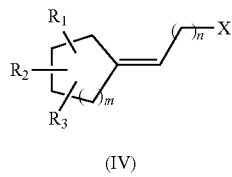

(IV)

$R_1$, $R_2$, $R_3$, n and m being as defined above and X representing a nitrile, carboxylic ester or alcohol function; and ii) converting the function X of the compound (IV) obtained into aldehyde, by reduction and/or oxidation, as a result of which the compound of formula (I) is obtained.

According to one embodiment, the method according to the invention comprises at least the following steps:

a step of adding a phosphorous ylide onto a cycloalkanone to obtain an intermediate compound, said phosphorus ylide comprising:
  in total 3 carbons and a nitrile function, to obtain a compound of formula I for which the side chain comprises in total 4 carbons (n=2), or
  in total 5 carbons and an ester function to obtain a compound of formula I for which the side chain comprises in total 5 carbons (n=3), or
  in total 6 carbons and an alcohol function to obtain a compound of formula I for which the side chain comprises in total 6 carbons (n=4),
followed by one step or two steps consisting of converting said intermediate compound into the corresponding aldehyde by reduction and/or oxidation.

When the intermediate compound is a nitrile (n=2), the step which makes it possible to obtain the corresponding aldehyde I of the present invention consists in a reduction using diisobutylaluminium hydride, in accordance with the protocols known to the person skilled in the art.

When the intermediate compound is an ester (n=3), a saponification step makes it possible to obtain, in accordance with operating procedures known to the person skilled in the art, the corresponding alcohol. When the intermediate compound is an alcohol (n=3 or 4), the step which makes it possible to obtain the aldehyde I of the present invention consists in an oxidation, in accordance with operating procedures known to the person skilled in the art. For example, it is possible to note the use of TEMPO and sodium hypochlorite (Anelli Oxidation) or Swern or Dess-Martin oxidation, or the use of supported transition metals (carbon, in particular) in an oxygen or air atmosphere.

The last object of the invention is the use of at least one compound of formula (I) according to the invention with the exception of the compounds 6-cycloheptylidenehexanal, 4-(4-methylcyclohexylidene)-butanal, 4-(4-tert-butylcyclohexylidene)-butanal and 4-(3,3,5-trimethylcyclohexylidene)-butanal as a fragrancing agent or compound, as an odour-masking agent or as an odour-neutralising agent. The terms "fragrant", "fragrancing" are used here interchangeably to designate any organoleptic compound stimulating the sense of smell in a pleasant manner. The term "masking agent" or "masking" is understood to mean reducing or eliminating the perception of a bad odour generated by one or more molecules entering into the composition of a product.

Furthermore, said compound can be used alone or in combination with at least one other flavouring or perfuming ingredient and/or at least one solvent, and/or at least one additive. The additional fragrancing agent(s) can be compounds of formula (I) or other fragrancing agents known to the person skilled in the art, who will be able to make a selection depending upon the effect sought.

Generally, the compounds according to the invention will be used in the field of perfumery. "Perfumery" is understood to mean not only perfumery in the usual meaning of the term, but also the other fields in which the fragrance of the products is important. It may concern perfumery compositions in the usual meaning of the term, such as perfuming bases and concentrates, eaux de Cologne, eaux de toilette, perfumes and similar products; topical compositions—in particular cosmetics—such as face and body creams, talcum powders, hair oils, shampoos, hair lotions, bath salts and oils, shower and bath gels, toilet soaps, body antiperspirants and deodorants, shaving lotions and creams, soaps, creams, toothpastes, mouthwashes, ointments, and similar products; and cleaning products, such as softeners, detergents, washing powders, air fresheners, and similar products.

A particular embodiment of the invention resides in the use of a compound of formula (I) with the exception of the compounds 6-cycloheptylidenehexanal, 4-(4-methylcyclohexylidene)-butanal, 4-(4-tert-butylcyclohexylidene)-butanal and 4-(3,3,5-trimethylcyclohexylidene)-butanal to confer, modify or boost the organoleptic properties of a substance, of a composition or of an article.

"Organoleptic properties" is understood to mean any property likely to modify, improve or boost the organoleptic perception of a substance, a composition, or an article by a user. Thus, as a preferred example, the organoleptic agent according to the invention can consist in a perfuming agent likely to confer, modify, improve or boost the olfactive perception of a substance, a composition, or an article.

The general principle of the invention is based on the preparation and the use in perfumery of the compounds of formula I described above. The following examples illustrate a particular manner of preparing the compounds of the invention, as well as the olfactive profile of each of the compounds given by way of example (see table 1 for olfactive descriptions). These examples are only given for illustration purposes and must not be understood as limiting the general scope of the invention.

EXAMPLE 1

Preparation of 4-(2-pentylcyclopentylidene)-butanal

An equivalent of 4-chlorobutyronitrile and an equivalent of triphenylphosphine in dibutyl ether at 140° C. are placed in a flask. After 20 hours of agitation in these conditions, and once returned to ambient temperature, the 3-(cyanopropyl)-triphenylphosphonium chloride formed is filtered on a frit, rinsed with methyl tert-butyl ether (MTBE) then dried under vacuum.

1 equivalent of 3-(cyanopropyl)-triphenylphosphonium chloride and 1.2 equivalents of potassium tertio-butylate in dry THF are placed in a flask. This suspension is agitated at 60° C. for 2 hours. 1 equivalent of 2-pentylcyclopentanone is then added. Agitation is performed at 60° C. until at least 90% of the 2-pentylcyclopentanone has converted. The reaction medium is allowed to return to ambient temperature. It is then poured onto a 10% HCl solution. The phases are separated. The aqueous phase is extracted twice with MTBE. The combined organic phases are washed with a saturated aqueous sodium bicarbonate solution, and then with salt water. After drying on magnesium sulfate, filtration on paper and evaporation of the solvent, the crude product is placed in MTBE in the refrigerator overnight. The precipitate is filtered on a frit and rinsed with MTBE. The filtrate is concentrated and then the crude product, made up of two isomers of 4-(2-pentylcyclopentylidene)-butanenitrile in proportion 52:48, is distilled under reduced pressure (b.p.=98° C./0.5 torr).

1 equivalent of 4-(2-pentylcyclopentylidene)-butanenitrile in proportion 52:48 in toluene at around 10° C. is then placed in a flask. 1.2 equivalents of a 1.0 M solution of Dibal (Diisobutylaluminium hydride) in toluene are added slowly, so as to keep the temperature of the solution below 40° C. At the end of the addition, the mixture is brought to 70° C. for 2 hours, and then left to cool at ambient temperature. The reaction medium is gently poured, with agitation, into an acetic acid/ice mixture. The phases are separated. The aqueous phase is extracted 3 times with MTBE. The combined organic phases are washed with a saturated sodium bicarbonate solution, and then with salt water. After drying on magnesium sulfate, filtration on paper and evaporation of the solvent, the crude product, containing two isomers in proportion 52:48 of 4-(2-pentylcyclopentylidene)-butanal, is deresined by molecular distillation before being distilled more finely under reduced pressure: its boiling point is 75° C. at 0.4 torr.

The 4-(2-pentylcyclopentylidene)-butanal thus obtained exhibits the following spectral characteristics:
Majority Isomer (52%):
MS [e/m (%)]: 208 (M+, 2), 164 (42), 149 (10), 147 (17), 138 (11), 137 (17), 135 (48), 134 (65), 133 (18), 121 (45), 120 (25), 119 (54), 110 (12), 109 (31), 108 (28), 107 (30), 105 (15), 97 (32), 96 (20), 95 (74), 94 (52), 93 (79), 92 (19), 91 (94), 83 (10), 82 (32), 81 (81), 80 (22), 79 (93), 78 (11), 77 (48), 69 (16), 68 (13), 67 (100), 65 (19), 57 (10), 55 (60), 53 (24), 43 (27), 41 (82), 39 (30).
$^{13}$C-NMR (50 MHz, CDCl$_3$): δ (ppm) 14.12, 22.07, 22.75, 23.98, 30.34, 31.87, 32.05, 33.38, 34.95, 40.29, 44.23, 118.01, 149.15, 202.58.
Minority Isomer (48%):
MS [e/m (%)]: 208 (M+, 23), 164 (39), 147 (17), 137 (18), 135 (46), 134 (65), 133 (18), 121 (44), 120 (27), 119 (60), 110 (13), 109 (30), 108 (29), 107 (29), 105 (17), 97 (33), 96 (20), 95 (79), 94 (55), 93 (86), 92 (20), 91 (100), 82 (32), 81 (84), 80 (22), 79 (97), 78 (13), 77 (50), 69 (16), 68 (12), 67 (100), 65 (19), 57 (10), 55 (63), 53 (25), 43 (28), 41 (85), 39 (29).
$^{13}$C-NMR (50 MHz, CDCl$_3$): δ (ppm) 14.12, 22.37, 22.71, 24.09, 29.28, 30.34, 32.16, 32.71, 34.44, 43.90, 44.34, 117.11, 148.79, 202.73.
2 Superimposed Isomers:
$^1$H-NMR (200 MHz, CDCl$_3$): δ (ppm) 0.89 (t, J=8.0 Hz, 3H), 1.28 (m, 7H), 1.43-1.63 (m, 3H), 1.70-1.91 (m, 2H), 2.18-2.40 (m, 4H), 2.45-2.53 (m, 3H), 5.10-5.17 (m, 1H), 9.77 (superimposed 2t, J=2.0 Hz, 1H).
IR (film, cm$^{-1}$): 839w, 1053w, 1379w, 1466m, 1726s, 2714w, 2856m, 2926s, 2953s.

EXAMPLE 2

Preparation of
4-(3,3-dimethylcyclohexylidene)-butanal 4-(3,3-dimethylcyclohexylidene)-butanal is prepared according to the protocol described in Example using 3,3-dimethylcyclohexanone in place of 2-pentylcyclopentanone. The crude product made up of two isomers of 4-(3,3,-dimethylcyclohexylidene)-butanal, in proportion 74:26, is distilled under reduced pressure: its boiling point is 85° C. at 0.4 torr.

The 4-(3,3-dimethylcyclohexylidene)-butanal thus obtained exhibits the following spectral characteristics:
Majority Isomer (74%):
$^1$H-NMR (200 MHz, CDCl$_3$): δ (ppm) 0.84 (s, 6H), 1.33-1.36 (m, 2H), 1.43-1.56 (m, 2H), 1.82 (s, 2H), 1.96-2.10 (m, 2H), 2.29-2.51 (m, 4H), 5.00 (t, J=7.0 Hz, 1H), 9.76 (t, J=2.0 Hz, 1H).
$^{13}$C-NMR (50 MHz, CDCl$_3$): δ (ppm) 20.02, 22.88, 27.88, 28.07, 36.34, 39.30, 44.07, 49.99, 120.04, 138.88, 202.37.
MS [e/m (%)]: 180 (M+, 1), 165 (12), 162 (26), 147 (38), 137 (11), 136 (32), 121 (35), 119 (12), 109 (39), 107 (19), 105 (15), 97 (18), 96 (10), 95 (25), 93 (40), 91 (27), 82 (13), 81 (56), 80 (13), 79 (36), 77 (25), 70 (10), 69 (100), 68 (20), 67 (37), 65 (12), 55 (40), 53 (22), 43 (14), 41 (72), 39 (28).
Minority Isomer (26%):
$^1$H-NMR (200 MHz, CDCl$_3$): δ (ppm) 0.88 (s, 6H), 1.33-1.36 (m, 2H), 1.43-1.56 (m, 2H), 1.91 (s, 2H), 1.96-2.10 (m, 2H), 2.29-2.51 (m, 4H), 5.15 (t, J=7.0 Hz, 1H), 9.76 (t, J=2.0 Hz, 1H).
$^{13}$C-NMR (50 MHz, CDCl$_3$): δ (ppm) 19.79, 23.81, 28.21, 32.42, 35.57, 39.51, 41.61, 49.99, 120.12, 139.06, 202.37.
MS [e/m (%)]: 180 (M+, 1), 162 (24), 147 (35), 136 (29), 121 (33), 119 (12), 109 (36), 107 (15), 105 (15), 97 (18), 95 (22), 93 (38), 91 (24), 82 (10), 81 (48), 80 (11), 79 (31), 77 (21), 70 (10), 69 (100), 68 (18), 67 (31), 65 (10), 55 (38), 53 (18), 43 (12), 41 (65), 39 (23).
IR (film, cm$^{-1}$): 859w, 975w, 1053w, 1365m, 1456m, 1725s, 2715w, 2841m, 2865m, 2925s, 2948s.

EXAMPLE 3

Preparation of
4-(2,4,4-trimethylcyclopentylidene)-butanal

The 4-(2,4,4-trimethylcyclopentylidene)-butanal is prepared according to the protocol described in Example 1 using 2,4,4-trimethylcyclopentanone in place of 2-pentylcyclopentanone. The crude product made up of two isomers of 4-(2,4,4-trimethylcyclopentylidene)-butanal in proportions 70:30, is distilled under reduced pressure: its boiling point is 70° C. at 0.4 torr.

The 4-(2,4,4-trimethycyclopentylidene)-butanal thus obtained exhibits the following spectral characteristics:
Majority Isomer (70%):
$^1$H-NMR (200 MHz, CDCl$_3$): δ (ppm) 1.02 (s, 6H), 0.91-1.06 (superimposed d, 3H), 1.10-1.15 (m, 1H), 1.64-1.86 (m, 2H), 2.02-2.47 (m, 5H), 2.62-2.80 (m, 1H), 5.07-5.12 (m, 1H), 9.76 (t, J=1.6 Hz, 1H).
$^{13}$C-NMR (50 MHz, CDCl$_3$): δ (ppm) 21.34, 21.43, 26.83, 28.81, 33.85, 37.69, 44.15, 48.96, 50.00, 118.90, 149.58, 202.49.
MS [e/m (%)]: 180 (M+, 1), 162 (18), 147 (41), 137 (13), 136 (68), 123 (12), 122 (11), 121 (100), 119 (13), 111 (16), 109 (34), 107 (19), 105 (15), 97 (11), 95 (37), 93 (33), 91 (28), 81 (37), 79 (33), 77 (26), 69 (15), 68 (12), 67 (32), 65 (11), 55 (34), 53 (20), 43 (12), 41 (47), 39 (25).
Minority Isomer (30%):
$^1$H-NMR (200 MHz, CDCl$_3$): δ (ppm) 0.81 (s, 6H), 0.91-1.06 (superimposed d, 3H), 1.10-1.15 (m, 1H), 1.64-1.86 (m, 2H), 2.02-2.47 (m, 5H), 2.62-2.80 (m, 1H), 5.07-5.12 (m, 1H), 9.76 (t, J=1.6 Hz, 1H).
$^{13}$C-NMR (50 MHz, CDCl$_3$): δ (ppm) 19.40, 22.32, 28.06, 29.51, 37.02, 37.12, 43.84, 44.46, 49.73, 117.57, 149.61, 202.62.
MS [e/m (%)]: 180 (M+, 1), 162 (18), 147 (37), 137 (14), 136 (72), 123 (12), 122 (11), 121 (100), 119(12), 109 (34), 107 (18), 105 (14), 97 (10), 95 (36), 93 (31), 91 (27), 81 (35), 79 (31), 77 (24), 69 (14), 68 (11), 67 (30), 65 (11), 55 (32), 53 (18), 43 (12), 41 (44), 39 (23).

IR (film, cm$^{-1}$): 830w, 1365m, 1460m, 1725s, 2716w, 2866m, 2927s, 2951s.

EXAMPLE 4

Preparation of 5-(2,4,4-trimethylcyclopentylidene)-pentanal

An equivalent of 5-bromopentanol and an equivalent of triphenylphosphine in refluxed ethanol are placed in a flask. After 72 hours of agitation in these conditions, and once returned to ambient temperature, the ethanol is evaporated under vacuum and the residue is placed into toluene at 4° C. overnight. The (5-hydroxypentyl)triphenylphosphonium bromide formed is filtered on a frit, rinsed with methyl tert-butyl ether then dried under vacuum.

1 equivalent of (5-hydroxypentyl)triphenylphosphonium bromide and 1.2 equivalents of potassium tertio-butylate in dry toluene are placed in a flask. This suspension is agitated at 70° C. for 2 hours. It is then returned to ambient temperature before the 2,4,4-trimethylcyclopentanone is added. Agitation is performed at 70° C. until at least 90% is converted. The reaction medium is allowed to return to ambient temperature. It is then poured onto a 10% HCl solution. The phases are separated. The organic phase is washed with a saturated aqueous sodium bicarbonate solution, and then with salt water. After drying on magnesium sulfate, filtration on paper and evaporation of the solvent, the crude product is placed in MTBE in the refrigerator overnight. The precipitate is filtered on a frit and rinsed with MTBE. The filtrate is concentrated and then the crude product, made up of two isomers of 5-(2,4,4-trimethylcyclopentylidene)-pentan-1-ol in proportion 68:32, is distilled under reduced pressure (b.p.=66° C./0.2 torr).

Thereafter 2.5 equivalents of PDC (pyridinium dichromate) and 1 equivalent of 5-(2,4,4-trimethylcyclopentylidene)-pentan-1-ol in proportion 68:32 in dichloromethane are placed in the flask. The suspension is agitated vigorously at ambient temperature overnight. When the conversion is satisfactory (>95%), the reaction medium is filtered on Celite® and then on silica. The filtrate thus obtained is washed with an aqueous 1% HCl solution and then with a saturated aqueous sodium bicarbonate solution, and then with water. After drying on magnesium sulfate, filtration on paper and evaporation of the solvent, the crude product, containing two isomers in proportion 68:32 of 5-(2,4,4-trimethylcyclopentylidene)-pentanal, is distilled under reduced pressure: its boiling point is 52° C. at 0.3 torr.

The 5-(2,4,4-trimethylcyclopentylidene)-pentanal thus obtained exhibits the following spectral characteristics:

Majority Isomer (68%):

$^1$H-NMR (200 MHz, CDCl$_3$): δ (ppm) 0.84 (s, 3H), 1.02-1.06 (superimposed s, 6H), 1.11-1.17 (m, 1H), 1.64-1.77 (m, 4H), 1.81-2.08 (m, 3H), 2.40-2.45 (m, 2H), 2.66-2.64 (m, 1H), 5.09-5.16 (m, 1H), 9.77 (t, J=1.8 Hz, 1H).

$^{13}$C-NMR (50 MHz, CDCl$_3$): δ (ppm) 21.21, 22.41, 26.88, 27.69, 28.82, 33.82, 36.94, 43.37, 49.02, 50.03, 120.13, 149.08, 202.73.

MS [e/m (%)]: 194 (M+, 12), 179 (29), 176 (13), 161 (61), 151 (21), 150 (66), 137 (10), 135 (80), 133 (22), 123 (24), 121 (25), 119 (31), 111 (16), 110 (12), 109 (56), 108 (15), 107 (38), 105 (19), 96 (10), 95 (100), 94 (18), 93 (36), 91 (35), 83 (25), 82 (13), 81 (67), 80 (10), 79 (72), 77 (33), 70 (10), 69 (34), 68 (10), 67 (47), 65 (14), 57 (10), 55 (42), 53 (24), 43 (16), 41 (56), 39 (22).

Minority Isomer (32%):

$^1$H-NMR (200 MHz, CDCl$_3$): δ (ppm) 0.93 (s, 3H), 1.02-1.06 (superimposed s, 6H), 1.11-1.17 (m, 1H), 1.64-1.77 (m, 4H), 1.81-2.08 (m, 3H), 2.40-2.45 (m, 2H), 2.66-2.64 (m, 1H), 5.33-5.40 (1H), 9.77 (t, J=1.8 Hz, 1H).

$^{13}$C-NMR (50 MHz, CDCl$_3$): δ (ppm) 19.51, 22.15, 28.04, 28.67, 29.51, 37.09, 37.64, 43.28, 44.48, 49.76, 118.70, 149.33, 202.73.

MS [e/m (%)]: 194 (M+, 13), 179 (31), 176 (145), 161 (69), 151 (20), 150 (64), 137 (11), 135 (76), 133 (24), 123 (24), 121 (24), 119 (36), 111 (20), 110 (12), 109 (59), 108 (17), 107 (38), 105 (22), 95 (100), 94 (17), 93 (37), 91 (38), 83 (24), 82 (12), 81 (70), 79 (72), 77 (35), 70 (12), 69 (37), 68 (12), 67 (46), 65 (14), 57 (10), 55 (41), 53 (25), 43 (17), 41 (58), 39 (26).

IR (film, cm$^{-1}$): 838w, 1365m, 1459m, 1726s, 2715w, 2866m, 2928s, 2951s.

EXAMPLE 5

Preparation of 5-cycloheptylidenepentanal

An equivalent of 5-bromopentyl pivalate and an equivalent of triphenylphosphine in toluene at 110° C. are placed in a flask. After 72 hours of agitation in these conditions, and once returned to ambient temperature, the toluene is evaporated and the triphenyl(5-(pivaloyloxy)pentyl)phosphonium bromide formed is used directly for the following step.

1 equivalent of triphenyl(5-(pivaloyloxy)pentyl)phosphonium bromide and 1.2 equivalents of potassium tertio-butylate in dry THF are placed in a flask. This suspension is agitated at 60° C. for 2 hours. Cycloheptanone is then added. Agitation is performed at 60° C. until at least 90% is converted. The reaction medium is allowed to return to ambient temperature, and then is poured onto a 10% HCl solution. The phases are separated. The aqueous phase is extracted twice with MTBE. The organic phases are washed with a saturated aqueous sodium bicarbonate solution, and then with salt water. After drying on magnesium sulfate, filtration on paper and evaporation of the solvent, the crude product is placed in MTBE in the refrigerator overnight. The precipitate is filtered on a frit and rinsed with MTBE. The filtrate is concentrated and then the crude product, made up of 5-cycloheptylidenepentyl, is distilled under reduced pressure (b.p.=104° C./0.7 torr).

The 5-cycloheptylidenepentyl pivalate is then placed in ethanol reflux with 0.1 equivalent of potassium hydroxide for twenty hours. The reaction medium is then allowed to return to ambient temperature. It is then poured onto a 10% HCl solution. The phases are separated. The aqueous phase is extracted twice with MTBE. The organic phases are washed with a saturated aqueous sodium bicarbonate solution, and then with salt water. After drying on magnesium sulfate, filtration on paper and evaporation of the solvent, the crude product, made up of 5-cycloheptylidenepentan-1-ol, is distilled under reduced pressure (b.p.=78° C./0.6 torr.

The alcohol thus obtained is then oxidised (see for example the last step of Example 4) to give 5-cycloheptylidenepentanal after purification under reduced pressure: its boiling point is 80° C. at 0.4 torr.

The 5-cycloheptylidenepentanal thus obtained exhibits the following spectral characteristics:

$^1$H-NMR (200 MHz, CDCl$_3$): δ (ppm) 0.93 (s, 3H), 1.02-1.06 (superimposed s, 6H), 1.11-1.17 (m, 1H), 1.64-1.77 (m, 4H), 1.81-2.08 (m, 3H), 2.40-2.45 (m, 2H), 2.66-2.64 (m, 1H), 5.33-5.40 (1H), 9.77 (t, J=1.8 Hz, 1H).

$^{13}$C-NMR (50 MHz, CDCl$_3$): δ (ppm) 19.51, 22.15, 28.04, 28.67, 29.51, 37.09, 37.64, 43.28, 44.48, 49.76, 118.70, 149.33, 202.73.

MS [e/m (%)]: 180 (M+, 3), 162 (14), 137 (11), 136 (69), 121 (64), 111 (16), 108 (40), 107 (39), 98 (13), 96 (10), 95 (58), 94 (31), 93 (39), 91 (21), 82 (42), 81 (94), 80 (23), 79 (64), 77 (27), 69 (22), 68 (28), 67 (100), 66 (10), 65 (15), 55 (59), 54 (23), 53 (29), 41 (76), 39 (36).

IR (film, cm$^{-1}$): 1057w, 1442m, 1724s, 2713w, 2850m, 2919s.

EXAMPLE 6

Preparation of 5-(4,4-diethylcyclohexylidene)-pentanal 5-(4,4-diethylcyclohexylidene)-pentanal is prepared according to the protocol described in Example using 4,4-diethylcyclohexanone in place of cycloheptanone. The crude product is distilled under reduced pressure: its boiling point is 80° C. at 0.4 torr.

The 5-(4,4-diethylcyclohexylidene)-pentanal thus obtained exhibits the following spectral characteristics:

$^1$H-NMR (200 MHz, CDCl$_3$): δ (ppm) 0.93 (s, 3H), 1.04-1.06 (superimposed s, 6H), 1.34-1.46 (m, 2H), 1.56-2.05 (m, 7H), 2.16-2.23 (m, 1H), 2.43 (t, J=7.4 Hz, 2H), 2.66 (q, J=7.0 Hz, 1H), 5.10-5.18 (m, 1H), 9.75 (t, J=1.8 Hz, 1H).

$^{13}$C-NMR (50 MHz, CDCl$_3$): δ (ppm) 19.49, 21.59, 26.81, 28.79, 28.97, 29.14, 36.85, 36.97, 44.39, 48.94, 49.78, 119.67, 148.15, 202.34.

MS [e/m (%)]: 208 (M+, 19), 193 (59), 176 (13), 175 (84), 165 (22), 147 (15), 135 (12), 133 (11), 125 (10), 124 (10), 123 (44), 122 (13), 121 (21), 119 (20), 111 (10), 110 (16), 109 (99), 108 (14), 107 (38), 105 (15), 95 (100), 93 (42), 91 (33), 84 (15), 83 (16), 82 (16), 81 (69), 80 (13), 79 (38), 77 (32), 69 (33), 67 (46), 66 (11), 55 (28), 53 (18), 52 (10), 43 (15), 41 (41), 39 (14).

IR (film, cm$^{-1}$): 844w, 1365m, 1459m, 1727s, 2714w, 2865m, 2927s, 2950s.

EXAMPLE 7

Preparation of 6-(2,4,4-trimethylcyclopentylidene)-hexanal

An equivalent of bromohexyl acetate and an equivalent of triphenylphosphine are placed in ethanol reflux in a flask. After 72 hours of agitation in these conditions, and once returned to ambient temperature, the ethanol and the ethyl acetate formed are evaporated under vacuum and the residue is placed into toluene at 4° C. overnight. The (6-hydroxypentyl)triphenylphosphonium bromide formed is filtered on a frit, rinsed with methyl tert-butyl ether (MTBE) then dried under vacuum.

1 equivalent of (6-hydroxyhexyl)triphenylphosphonium bromide and 1.2 equivalents of potassium tertio-butylate in dry toluene are placed in a flask. This suspension is agitated at 70° C. for 2 hours, and then 2,4,4-trimethylcyclopentanone is added. Agitation is performed at 70° C. until at least 90% is converted. The reaction medium is allowed to return to ambient temperature. It is then poured onto a 10% HCl solution. The phases are separated. The organic phase is washed with a saturated aqueous sodium bicarbonate solution, and then with salt water. After drying on magnesium sulfate, filtration on paper and evaporation of the solvent, the crude product is placed in MTBE in the refrigerator overnight. The precipitate is filtered on a frit and rinsed with MTBE. The filtrate is concentrated and then the crude product, made up of two isomers of 6-(2,4,4-trimethylcyclopentylidene)-hexan-1-ol in proportion 70:30, is distilled under reduced pressure (b.p.=89° C./0.1 torr).

Thereafter 2.5 equivalents of PDC (pyridinium dichromate) and 1 equivalent of 6-(2,4,4-trimethylcyclopentylidene)-hexan-1-ol in proportion 70:30 in dichloromethane are placed in a flask. The suspension is agitated vigorously at ambient temperature overnight. When the conversion is satisfactory (>95%), the reaction medium is filtered on Celite® and then on silica. The filtrate thus obtained is washed with an aqueous 1% HCl solution and then with a saturated aqueous sodium bicarbonate solution, and then with water. After drying on magnesium sulfate, filtration on paper and evaporation of the solvent, the crude product, containing two isomers in proportion 70:30 of 6-(2,4,4-trimethylcyclopentylidene)-hexanal, is distilled under reduced pressure: its boiling point is 59° C. at 0.2 torr.

The 6-(2,4,4-trimethylcyclopentylidene)-hexanal thus obtained exhibits the following spectral characteristics:

Majority Isomer (70%):

$^1$H-NMR (200 MHz, CDCl$_3$): δ (ppm) 0.83 (s, 3H), 1.04-1.06 (s superimposed, 6H), 1.34-1.46 (m, 2H), 1.56-2.05 (m, 7H), 2.16-2.23 (m, 1H), 2.42 (t, J=7.2 Hz, 2H), 2.66 (q, J=7.0 Hz, 1H), 5.10-5.18 (m, 1H), 9.75 (t, J=1.8 Hz, 1H).

$^{13}$C-NMR (50 MHz, CDCl$_3$): δ (ppm) 21.45, 21.67, 26.81, 28.03, 28.79, 29.47, 33.74, 37.58, 43.70, 48.94, 50.04, 120.81, 147.99, 202.29.

MS [e/m (%)]: 208 (M+, 8), 194 (10), 193 (50), 190 (22), 175 (63), 165 (18), 147 (14), 137 (13), 133 (13), 124 (11), 123 (55), 122 (12), 121 (25), 119 (18), 110 (18), 109 (74), 108 (16), 107 (25), 105 (20), 95 (100), 93 (36), 91 (31), 83 (12), 81 (52), 79 (41), 77 (25), (32), 68 (10), 67 (33), 65 (13), 55 (30), 53 (19), 43 (16), 41 (52), 39 (16).

Minority Isomer (30%):

$^1$H-NMR (200 MHz, CDCl$_3$): δ (ppm) 0.93 (s, 3H), 1.04-1.06 (superimposed s, 6H), 1.34-1.46 (m, 2H), 1.56-2.05 (m, 7H), 2.16-2.23 (m, 1H), 2.43 (t, J=7.4 Hz, 2H), 2.66 (q, J=7.0 Hz, 1H), 5.10-5.18 (m, 1H), 9.75 (t, J=1.8 Hz, 1H).

$^{13}$C-NMR (50 MHz, CDCl$_3$): δ (ppm) 19.49, 21.59, 26.81, 28.79, 28.97, 29.14, 36.85, 36.97, 44.39, 48.94, 49.78, 119.67, 148.15, 202.34.

MS [e/m (%)]: 208 (M+, 19), 193 (59), 176 (13), 175 (84), 165 (22), 147 (15), 135 (12), 133 (11), 125 (10), 124 (10), 123 (44), 122 (13), 121 (21), 119 (20), 111 (10), 110 (16), 109 (99), 108 (14), 107 (38), 105 (15), 95 (100), 93 (42), 91 (33), 84 (15), 83 (16), 82 (16), 81 (69), 80 (13), 79 (38), 77 (32), 69 (33), 67 (46), 66 (11), 55 (28), 53 (18), 52 (10), 43 (15), 41 (41), 39 (14).

IR (film, cm$^{-1}$): 844w, 1365m, 1459m, 1727s, 2714w, 2865m, 2927s, 2950s.

EXAMPLE 8

Preparation of the 6-(2-methylcyclohexylidene)-hexanal 6-(2-methylcyclohexylidene)-hexanal is prepared according to the protocol described in Example 7 using 2-methylcyclohexanone in place of 2,4,4-trimethylcyclopentanone. The crude product, made up of two isomers in proportion 70:30, is distilled under reduced pressure: its boiling point is 71° C. at 0.3 torr.

The 6-(2-methylcyclohexylidene)-hexanal thus obtained exhibits the following spectral characteristics:

Majority Isomer (70%):

$^1$H-NMR (200 MHz, CDCl$_3$): δ (ppm) 0.99-1.06 (superimposed d, 3H), 1.33-1.44 (m, 5H), 1.48-1.71 (m, 7H), 1.98-2.09 (m, 3H), 2.44 (td, J=6.0 Hz, J=1.8 Hz, 2H), 4.96-5.06 (m, 1H), 9.76 (t, J=1.8 Hz, 1H).

$^{13}$C-NMR (50 MHz, CDCl$_3$): δ (ppm) 18.63, 21.63, 25.45, 28.10, 28.15, 29.70, 36.74, 38.37, 43.77, 117.90, 144.07, 202.73.

MS [e/m (%)]: 194 (M+, 9), 176 (15), 161 (20), 147 (15), 110 (10), 109 (50), 108 (22), 107 (11), 97 (12), 96 (67), 95 (81), 94 (14), 93 (25), 91 (19), 82 (15), 81 (100), 80 (13), 79 (25), 77 (18), 69 (14), 68 (15), 67 (75), 65 (11), 55 (44), 53 (16), 41 (39), 39 (17).

Minority Isomer (30%):

$^1$H-NMR (200 MHz, CDCl$_3$): δ (ppm) 0.99-1.06 (superimposed d, 3H), 1.33-1.44 (m, 5H), 1.48-1.71 (m, 7H), 1.98-2.09 (m, 3H), 2.44 (td, J=6.0 Hz, J=1.8 Hz, 2H), 4.96-5.06 (m, 1H), 9.76 (t, J=1.8 Hz, 1H).

$^{13}$C-NMR (50 MHz, CDCl$_3$): δ (ppm) 18.12, 20.93, 26.38, 26.69, 28.56, 29.62, 30.13, 32.44, 33.19, 120.55, 143.59, 202.73.

MS [e/m (%)]: 194 (M+, 5), 176 (19), 161 (21), 147 (17), 133 (12), 110 (10), 109 (47), 108 (22), 107 (11), 97 (13), 96 (39), 95 (76), 94 (15), 93 (27), 91 (19), 82 (14), 81 (100), 80 (12), 79 (41), 77 (18), 69 (14), 68 (15), 67 (75), 55 (45), 53 (16), 41 (41), 39 (15).

IR (film, cm$^{-1}$): 896w, 1368w, 1456m, 1725s, 2714w, 2852m, 2923s.

EXAMPLE 9

Preparation of 6-(4-methylcyclohexylidene)-hexanal 6-(4-methylcyclohexylidene)-hexanal is prepared according to the protocol described in Example 7 using 4-methylcyclohexanone in place of 2,4,4-trimethylcyclopentanone. The crude product containing 6-(4-methylcyclohexylidene)-hexanal is distilled under reduced pressure: its boiling point is 69° C. at 0.35 torr.

The 6-(4-methylcyclohexylidene)-hexanal thus obtained exhibits the following spectral characteristics:

$^1$H-NMR (200 MHz, CDCl$_3$): δ (ppm) 0.89 (d, J=6.6 Hz, 3H), 0.98-1.02 (m, 1H), 1.35-1.40 (m, 3H), 1.58-1.77 (m, 6H), 1.99-2.11 (m, 4H), 2.42-2.57 (m, 3H), 5.05 (t, J=7.2 Hz, 2H), 9.76 (s, 1H).

$^{13}$C-NMR (50 MHz, CDCl$_3$): δ (ppm) 21.59, 22.05, 26.78, 27.88, 29.58, 32.84, 35.97, 36.41, 36.81, 43.77, 120.67, 139.63, 202.71.

MS [e/m (%)]: 194 (M+, 5), 176 (35), 161 (13), 147 (19), 135 (10), 123 (13), 109 (11), 108 (13), 107 (14), 96 (10), 95 (65), 94 (22), 93 (30), 91 (18), 82 (10), 81 (100), 80 (12), 79 (40), 77 (22), 69 (13), 68 (21), 67 (55), 65 (12), 55 (36), 53 (17), 41 (40), 39 (18).

IR (film, cm$^{-1}$): 847w, 1081w, 1373w, 1456m, 1725s, 2714w, 2846m, 2912s 2948s.

EXAMPLE 10

Preparation of 6-(4-tert-butylcyclohexylidene)-hexanal 6-(4-tert-butylcyclohexylidene)-hexanal is prepared according to the protocol described in Example 7 using 4-tert-butylcyclohexanone in place of 2,4,4-trimethylcyclopentanone. The crude product containing 6-(4-tert-butylcyclohexylidene)-hexanal is distilled under reduced pressure: its boiling point is 100° C. at 0.3 torr.

The 6-(4-tert-butylcyclohexylidene)-hexanal thus obtained exhibits the following spectral characteristics:

$^1$H-NMR (200 MHz, CDCl$_3$): δ (ppm) 1.03 (s, 9H), 1.10-1.16 (m, 2H), 1.32-1.44 (m, 3H), 1.56-1.68 (m, 3H), 1.80-1.86 (m, 2H), 1.99-2.03 (m, 3H), 2.16-2.24 (m, 1H), 2.42 (td, J=7.2 Hz, J=1.8 Hz, 2H), 2.61 (dq, J=13.6 Hz, J=2.4 Hz, 1H), 5.04 (t, J=7.2 Hz, 1H), 9.76 (t, J=1.8 Hz, 1H).

$^{13}$C-NMR (50 MHz, CDCl$_3$): δ (ppm) 21.63, 26.77, 27.59, 28.42, 28.47, 29.23, 29.59, 32.41, 36.96, 43.78, 48.46, 120.19, 140.03, 202.78.

MS [e/m (%)]: 236 (M+, 8), 218 (18), 179 (11), 162 (20), 147 (20), 135 (11), 133 (12), 123 (13), 121 (10), 119 (17), 109 (25), 107 (10), 105 (15), 97 (12), 96 (13), 95 (44), 94 (15), 93 (30), 92 (10), 91 (29), 83 (14), 82 (12), 81 (48), 80 (20), 79 (65), 77 (30), 69 (17), 67 (46), 65 (10), 57 (100), 55 (31), 53 (12), 43 (19), 41 (60), 39 (12).

IR (film, cm$^{-1}$): 848w, 1365m, 1443m, 1726s, 2714w, 2861m, 2940s.

EXAMPLE 11

Preparation of 6-(4-tert-amylcyclohexylidene)-hexanal 6-(4-tert-amylcyclohexylidene)-hexanal is prepared according to the protocol described in Example 7 using 4-tert-amylcyclohexanone in place of 2,4,4-trimethylcyclopentanone. The crude product containing 6-(4-tert-amylcyclohexylidene)-hexanal is purified on a silica column by an eluent made up of 5% hexane and 95% ethyl acetate.

The 6-(4-tert-amylcyclohexylidene)-hexanal thus obtained exhibits the following spectral characteristics:

$^1$H-NMR (200 MHz, CDCl$_3$): δ (ppm) 0.78 (s, 6H), 0.80 (t, J=7.0 Hz, 3H), 1.00 (qd, J=12.0 Hz, J=4.0 Hz, 2H), 2H), 1.20-1.40 (m, 6H), 1.56-1.68 (m, 3H), 1.71-1.80 (m, 3H), 1.99-2.05 (m, 3H), 2.16-2.65 (m, 2H), 2.42 (td, J=8.0 Hz, J=2.0 Hz, 2H), 5.03 (t, J=7.0 Hz, 1H), 9.76 (t, J=2.0 Hz, 1H).

$^{13}$C-NMR (50 MHz, CDCl$_3$): δ (ppm) 8.14, 21.67, 24.36, 26.81, 28.05, 28.59, 28.85, 29.64, 29.79, 32.74, 34.73, 37.09, 43.84, 45.66, 120.19, 140.18, 202.86.

MS [e/m (%)]: 250 (M+, 1), 162 (15), 161 (23), 147 (13), 119 (11), 109 (15), 105 (10), 95 (28), 94 (13), 93 (21), 91 (23), 81 (43), 80 (15), 79 (40), 77 (15), 71 (100), 70 (26), 69 (14), 67 (40), 55 (33), 53 (10), 43 (82), 41 (51), 39 (12).

EXAMPLE 12

Preparation of 6-cyclooctylidenehexanal 6-cyclooctylidenehexanal is prepared according to the protocol described in Example 7 using cyclooctane in place of 2,4,4-trimethylcyclopentanone. The crude product containing cyclooctylidenehexanal is distilled under reduced pressure: its boiling point is 94° C. at 0.2 torr.

The 6-cyclooctylidenehexanal thus obtained exhibits the following spectral characteristics:

$^1$H-NMR (200 MHz, CDCl$_3$): δ (ppm) 1.25-1.69 (m, 14H), 2.00-2.17 (m, 6H), 2.43 (td, J=10.0 Hz, J=2.0 Hz, 2H), 5.09-5.58 (m, 1H), 9.77 (t, J=2.0 Hz, 1H).

$^{13}$C-NMR (50 MHz, CDCl$_3$): δ (ppm) 19.74, 24.14, 26.30, 26.34, 26.57, 28.92, 29.21, 29.77, 32.04, 47.83, 65.58, 125.14, 142.69, 211.33.

MS [e/m (%)]: 208 (M+, 9), 190 (13), 162 (41), 161 (10), 147 (13), 135 (12), 133 (12), 122 (15), 121 (15), 110 (11), 109 (51), 108 (15), 107 (21), 97 (20), 96 (40), 95 (81), 94 (25), 93

(28), 91 (25), 84 (11), 83 (20), 82 (36), 81 (100), 80 (26), 79 (57), 77 (23), 70 (10), 69 (28), 68 (23), 67 (94), 65 (13), 55 (60), 54 (16), 53 (24), 43 (13), 41 (70), 39 (26).

IR (film, cm$^{-1}$): 971w, 1447m, 1468m, 1726s, 2712w, 2852m, 2920s.

EXAMPLE 13

Preparation of 6-(3,3-dimethylcyclohexylidene)hexanal 6-(3,3-dimethylcyclohexylidene)hexanal is prepared according to the protocol described in Example 7 using 3,3-dimethylcyclohexanone in place of 2,4,4-trimethylcyclopentanone. The crude product, made up of two isomers in proportion 60:40, is distilled under reduced pressure: its boiling point is 75° C. at 0.46 torr.

The 6-(3,3-dimethylcyclohexylidene)hexanal thus obtained exhibits the following spectral characteristics:

Majority Isomer (60%):
$^1$H-NMR (200 MHz, CDCl$_3$): δ (ppm) 0.82 (s, 6H), 1.25-1.5 (m, 6H), 1.5-1.75 (m, 3H), 1.79 (s, 2H), 1.9-2.1 (m, 3H), 2.40 (dt, J=7.36, 1.83 Hz, 2H), 4.97 (t, J=7.32 Hz, 1H), 9.73 (t, J=1.86 Hz, 1H).
$^{13}$C-NMR (50 MHz, CDCl$_3$): δ (ppm) 21.57; 23.19; 26.83; 28.10; 28.32; 29.61; 32.56; 39.62; 43.73; 50.36; 122.12; 137.81; 202.7.

Minority Isomer (40%):
$^1$H-NMR (200 MHz, CDCl$_3$): δ (ppm) 0.85 (s, 6H), 1.25-1.5 (m, 6H), 1.5-1.75 (m, 3H), 1.86 (s, 2H), 1.9-2.1 (m, 3H), 2.40 (dt, J=7.36, 1.83 Hz, 2H), 5.12 (tt, J=7.24 Hz, 1.1 Hz, 1H), 9.73 (t, J=1.86 Hz, 1H).
$^{13}$C-NMR (50 MHz, CDCl$_3$): δ (ppm) 21.72; 24.11; 26.76; 28.45; 29.61; 32.69; 36.66; 39.84; 41.87; 43.76; 122.23; 137.92; 202.7.

EXAMPLE 14

Perfuming Composition B Incorporating 6-(2,4,4-trimethylcyclopentylidene)hexanal Obtained According to Example 7

The comparative olfactive evaluation test extending to the study of the impact of the compounds given in various formulae is carried out as follows. The same formula or accord is produced on the one hand without any raw material belonging to the claimed compounds of formula (I), and on the other hand with one of the compounds of formula (I), at a dose which is suited to its olfactive power. The thus-prepared formulae or accords in turn undergo a blind comparative evaluation.

The following two accords were prepared: a tamarind accord A, then the same tamarind accord A further comprising 6-(2,4,4-trimethylcyclopentylidene)-hexanal to give accord B. Their formulations are described below and are used as perfuming bases: they are incorporated at 1% by weight in a ready-to-use shower gel.

| Ingredients | Accord A | Accord B |
|---|---|---|
| ALDEHYDE C08 | 0.05 | 0.05 |
| LINALOOL | 7.40 | 7.40 |
| LIMONENE | 28.00 | 28.00 |
| OXANE or 2-methyl-4-propyl-1,3-oxathiane (Firmenich, Switzerland) | 0.70 | 0.70 |
| PARACYMENE | 10.00 | 10.00 |
| THYMOL | 0.90 | 0.90 |
| C12 LAURIC ALDEHYDE | 0.15 | 0.15 |
| 1,3,5-UNDECATRIENE | 0.20 | 0.20 |
| METHYL METHYL ANTHRANILATE | 10.00 | 10.00 |
| DIPROPYLENE GLYCOL | 42.60 | 41.70 |
| 6-(2,4,4-trimethylcyclopentylidene)-hexanal | 0.00 | 0.90 |

The comparative evaluation of accords A and B at 1% by weight in shower gel base shows that the addition of 6-(2,4,4-trimethylcyclopentylidene)-hexanal at the level of 0.9% in accord B provides a notable and very advantageous effect: it accentuates the fruity mandarin facet of the core fragrance in particular, compared to accord A.

EXAMPLE 15

Perfuming Composition E Including 6-(2,4,4-trimethylcyclopentylidene)-hexanal Obtained According to Example 7

The comparative olfactive evaluation extending to the study of the impact of the compounds given in formulae is carried out in accordance with the test described in Example 7. In this example, a third formula was prepared integrating one of the raw materials which is olfactively comparable with the compounds of formula (I): Calone® (or 7-methyl-3,4-dihydro-2H-1,5-benzodioxepin-3-one), in the same dose.

Ladies' eaux de toilettes were prepared by incorporating 10% by weight of the three perfuming formulae described below, one of which contains 6-(2,4,4-trimethylcyclopentylidene)-hexanal and one of which contains Calone®:

| Ingredients | Accord C | Accord D | Accord E |
|---|---|---|---|
| GAMMA NONALACTONE | 0.05 | 0.05 | 0.05 |
| LEMON OIL | 2.00 | 2.00 | 2.00 |
| BERGAMOT OIL | 2.00 | 2.00 | 2.00 |
| COUMARIN | 0.30 | 0.30 | 0.30 |
| MUSK T ® or ethylene brassylate (Takasago, Japan) | 5.00 | 5.00 | 5.00 |
| BENZYL SALICYLATE | 18.00 | 18.00 | 18.00 |
| CIS-3-HEXENYL SALICYLATE | 3.00 | 3.00 | 3.00 |
| METHYL DIHYDROJASMONATE | 20.00 | 20.00 | 20.00 |
| VANILLIN | 0.50 | 0.50 | 0.50 |
| GALAXOLIDE ® or 1,3,4,6,7,8-hexahydro-4,6,6,7,8,8-hexamethylcyclopenta-(g)-2-benzopyrane (IFF, United States) | 20.00 | 20.00 | 20.00 |
| YLANG OIL | 1.50 | 1.50 | 1.50 |
| METHYL ANTHRANILATE | 0.10 | 0.10 | 0.10 |
| DIPROPYLENE GLYCOL | 27.55 | 25.55 | 25.55 |
| CALONE ® or 7-methyl-3,4-dihydro-2H-1,5-benzodioxepin-3-one (Pfizer and Co., United States). | 0.00 | 2.00 | 0.00 |
| 6-(2,4,4-trimethylcyclopentylidene)-hexanal | 0.00 | 0.00 | 2.00 |

Comparative evaluation of accords C, D and E at 10% by weight in alcohol base: addition of 2% of Calone® lends accord D a marine facet. Addition of 2% of 6-(2,4,4-trimethylcyclopentylidene)-hexanal in accord E lends a very interesting effect by giving potency to the perfume and in particular to the musky, sunny notes and by lending more roundness and powderiness compared to accord C.

EXAMPLE 16

Perfuming Composition G Incorporating 6-(2,4,4-trimethylcyclopentylidene)-hexanal Obtained According to Example 7

The comparative olfactive evaluation extending to the study of the impact of the compounds given in formulae is carried out in accordance with the test described in Example 7.

A lily of the valley-pear accord F, then the same accord comprising 6-(2,4,4-trimethylcyclopentylidene)-hexanal to give accord G the formulations of which are described below, are used as perfuming bases: they are prepared and then incorporated at 1% by weight in a ready-to-use softener:

| Ingredients | Accord F | Accord G |
|---|---|---|
| HEXYL ACETATE | 1.10 | 1.10 |
| DIHYDROMYRCENOL ® or 2,6-dimethyl-7-octen-2-ol (IFF, United States) | 0.20 | 0.20 |
| PHENYLETHYL ALCOHOL | 22.20 | 22.20 |
| LINALOOL | 6.70 | 6.70 |
| BENZYL ACETATE | 2.20 | 2.20 |
| STYRALLYL ACETATE | 0.20 | 0.20 |
| FRESKOMENTHONE | 0.30 | 0.30 |
| DIMETHYLBENZYL CARBINOL ACETATE | 0.10 | 0.10 |
| CYCLAMEN ALDEHYDE | 3.30 | 3.30 |
| LILIAL ® or para-tert-butyl-alpha-methylhydrocinnamaldehyde (Givaudan, Switzerland) | 11.00 | 11.00 |
| C14 ALDEHYDE | 0.70 | 0.70 |
| METHYL DIHYDROJASMONATE | 4.50 | 4.50 |
| CITRONELLOL | 13.50 | 13.50 |
| TERPINEOL | 2.20 | 2.20 |
| HELIOTROPIN | 0.80 | 0.80 |
| GALAXOLIDE ® or 1,3,4,6,7,8-hexahydro-4,6,6,7,8,8-hexamethylcyclopenta-(g)-2-benzopyrane (IFF, United States) | 5.50 | 5.50 |
| PHENOXANOL ® or 3-methyl-5-phenylpentan-1-ol (IFF, United States) | 1.70 | 1.70 |
| CINNAMIC ALDEHYDE | 0.20 | 0.20 |
| HEXYL CINNAMIC ALDEHYDE | 3.30 | 3.30 |
| TRIPLAL ® or 2,4-dimethyl-3-cyclohexen-1-carbaldehyde (IFF, United States) | 0.60 | 0.60 |
| METHYL ANTHRANILATE | 0.10 | 0.10 |
| DIPROPYLENE GLYCOL | 19.60 | 19.50 |
| 6-(2,4,4-trimethylcyclopentylidene)-hexanal | 0.00 | 0.10 |

The comparative evaluation of accords F and G at 1% by weight in softener base shows that the addition of only 0.1% of 6-(2,4,4-trimethylcyclopentylidene)-hexanal in softener base in accord G lends a very notable effect by accentuating the green, vegetable watery facet compared to accord F.

The invention claimed is:
1. A compound of the following general formula (I):

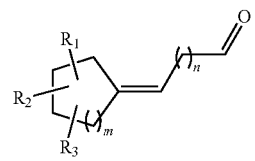

wherein:
R1, R2 and R3 each independently represent a hydrogen atom or a saturated or unsaturated, branched or non-branched C1-C5 alkyl group;
m is an integer between 1 and 4;
n is an integer between 2 and 4;
wherein the ring is saturated and comprises from 5 to 8 carbons, that the total number of carbons of the ring and of the radicals R1, R2 and R3 is between 7 and 11; and
wherein said compound of formula (I) is not:
6-cycloheptylidenehexanal
4-(4-methylcyclohexylidene)-butanal
4-(4-tert-butylcyclohexylidene)-butanal
4-(3,3,5-trimethylcyclohexylidene)-butanal
4-cyclooctylidene-butanal or
4-cycloheptylidene-butanal.
2. The compound according to claim 1, wherein m is equal to 1.
3. The compound according to claim 1, wherein n is equal to 4.
4. The compound according to claim 1, wherein n is equal to 2.
5. The compound according to claim 1, wherein the compound is selected from the group consisting of 5-(2,4,4-trimethylcyclopentylidene)-pentanal, 6-(2,4,4-trimethylcyclopentylidene)-hexanal, 6-(2-methylcyclohexylidene)-hexanal, 6-(4-methylcyclohexylidene)-hexanal, 6-(4-tert-butylcyclohexylidene)-hexanal, 6-(4-tert-amylcyclohexylidene)-hexanal, 6-cyclooctylidenehexanal, 6-(3,3-dimethylcyclohexylidene)hexanal, 4-(2,4,4-trimethylcyclopentylidene)butanal, 4-(2-pentylcyclopentylidene)-butanal, 4-(3,3-dimethylcyclohexylidene)-butanal, 5-(4,4-diethylcyclohexylidene)-pentanal and 5-cycloheptylidenepentanal.
6. A composition comprising at least one compound of general formula (I) as defined in claim 1 in the form of an isomer or a mixture of isomers, of an enantiomer or of a mixture of enantiomers, or of a racemic mixture, or of a diastereoisomer or of a mixture of diastereoisomers.
7. The composition according to claim 6, comprising at least one other fragrancing substance.
8. A method of preparing a compound of formula (I) as described in claim 1 in which a cycloalkanone and a phosphorus ylide undergo a Wittig reaction, followed by a reduction and/or oxidation step depending on the ylide used previously.
9. A method according to claim 8 comprising the steps of:
i) adding a phosphorus ylide of formula (III) onto a cycloalkanone of formula (II), in accordance with a Wittig reaction:
R1, R2 and R3 each independently representing a hydrogen atom or saturated or unsaturated, branched or non-branched C1-C5 alkyl group;
m being an integer between 1 and 4;

n being an integer between 2 and 4;

the ring being saturated, comprises from 5 to 8 carbons, the total number of carbons of the ring and of the radicals R1, R2 and R3 being between 7 and 11;

and X representing a nitrile, carboxylic ester or alcohol function; and ii) converting the function X of the compound (IV) obtained, into aldehyde, by reduction and/or oxidation.

10. A method of adding a fragrance to substance, composition or article comprising adding to said substance, composition or article at least one compound of formula (I) as defined in claim 1 as a fragrant agent or compound.

11. A method of masking or neutralizing an odor in a substance, composition or article comprising adding to said substance, composition, or article at least one compound of formula (I) as defined in claim 1 as an odor-masking or odor-neutralizing agent.

12. The method according to claim 10, wherein at least one compound of formula (I) is added in combination with at least one other flavouring or perfuming ingredient, and/or at least one solvent, and/or at least one additive.

13. The method according to claim 10 wherein the addition of said compound confers, modifies or boosts the organoleptic properties of said substance, a composition or article.

14. The method according to claim 10 wherein said method produces compositions selected from the group consisting of perfumery compositions, topical compositions, cosmetics, and cleaning products.

* * * * *